(12) United States Patent
Santarella et al.

(10) Patent No.: US 7,585,301 B2
(45) Date of Patent: Sep. 8, 2009

(54) MODULAR HIP INSERTER/POSITIONER

(75) Inventors: Michael Santarella, Essex Fells, NJ (US); Richard H. Pilsbury, Pine Brook, NJ (US); Martin M. Coyne, III, Ramsey, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 257 days.

(21) Appl. No.: 10/170,129

(22) Filed: Jun. 12, 2002

(65) Prior Publication Data

US 2003/0233100 A1 Dec. 18, 2003

(51) Int. Cl.
*A61B 17/56* (2006.01)
*A61F 2/32* (2006.01)

(52) U.S. Cl. .................. 606/99; 623/22.12

(58) Field of Classification Search .............. 606/99, 606/91, 86, 104; 623/20.35, 20.36, 22.12, 623/23.25, 23.34, 23.44
See application file for complete search history.

(56) References Cited

U.S. PATENT DOCUMENTS

| | | | |
|---|---|---|---|
| 5,409,492 A | 4/1995 | Jones et al. | |
| 5,571,111 A | 11/1996 | Aboczky | |
| 5,645,549 A | 7/1997 | Boyd et al. | |
| 5,913,860 A | 6/1999 | Scholl | |
| 6,033,405 A | 3/2000 | Winslow et al. | |
| 6,110,179 A | 8/2000 | Flivik et al. | |
| 6,110,211 A | 8/2000 | Weiss | |
| 6,117,173 A | 9/2000 | Taddia et al. | |
| 6,136,035 A * | 10/2000 | Lob et al. | ............. 623/23.15 |
| 6,143,030 A | 11/2000 | Schroder | |
| 6,224,609 B1 | 5/2001 | Ressemann et al. | |
| 6,238,435 B1 | 5/2001 | Meulink et al. | |
| 6,267,785 B1 | 7/2001 | Masini | |
| 6,302,890 B1 | 10/2001 | Leone, Jr. | |
| 6,330,845 B1 | 12/2001 | Meulink | |
| 6,344,060 B1 | 2/2002 | Schmotzer et al. | |
| 6,361,565 B1 | 3/2002 | Bonutti | |
| 6,371,991 B1 | 4/2002 | Manasas et al. | |

OTHER PUBLICATIONS

Biomet, Inc., Sundial Version Control Device, 1997 Form No. Y-BMT-502/013197/M.
Link America, Inc., The Link® MP Reconstruction Hip Stem, 1997, LIT MP-03 97.
ZMR™ Hip System, Revision Taper, Modular Hip Prosthesis.

* cited by examiner

*Primary Examiner*—Eduardo C Robert
*Assistant Examiner*—David Comstock
(74) *Attorney, Agent, or Firm*—Lerner, David, Littenberg, Krumholz & Mentlik, LLP (57) ABSTRACT

A modular hip body/stem inserter comprises a stem inserter and a holder. A proximal body portion of an implant is loaded, or mounted, onto the holder. A distal stem portion of the implant is affixed onto the stem inserter. The modular hip body/stem inserter maintains the proximal body portion and distal stem portion a short distance apart. The stem inserter can be adjusted to control the version of the distal stem, while the holder can be independently adjusted to control the version of the proximal body. Once the version is adjusted to determine a final seating position, the stem inserter portion is removed and the holder is then used to impact the proximal body and distal stem together, thereby locking the implant components together through a taper locking mechanism.

29 Claims, 9 Drawing Sheets

MODULAR HIP INSERTER/POSITIONER

BACKGROUND OF THE INVENTION

The invention relates generally to arthroplasty and, more particularly, to devices and techniques for positioning a prosthesis.

During the implantation of bowed orthopedic hip implants with fixed neck-bow orientation, there exists a tendency for the implant to rotate or corkscrew as it enters the bow of the femur. This causes an undesirable implant neck orientation otherwise referred to as neck version (hereafter, simply referred to as "version"). Currently available bowed modular implants do not address this situation as they are assembled outside the body with the version set based on trials prior to implementation. A variety of external assembly devices have been developed that set the final implant in the same version as that determined during trial (see, e.g., the Sundial Version Control device available from Biomet, Inc.).

In addition, the surgeon must estimate the degree of implant rotation and begin the implantation in an undesirable orientation with the expectation that the implant will be properly orientated at the completion of implantation. If optimal implant neck version is not attained, the surgeon must decide whether to leave the implant in a non-optimal orientation and risk possible dislocation, or extract the implant and re-implant.

SUMMARY OF THE INVENTION

In accordance with an aspect of the invention, a positioning tool for inserting an implant provides independent control of the orientation between a first component and a second component of the implant.

In an embodiment of the invention, a positioning tool comprises a first piece for engaging a first component of an implant and controlling an orientation thereof; a second piece for engaging a second component of the implant; and a third piece for controlling an orientation of the engaged second component such that the engaged first and second components of the implant do not lock together and wherein the first piece and the third piece provide independent version control for the first and second components of the implant.

In another embodiment of the invention, a modular hip body/stem inserter with independent version control of body and stem comprises two parts: a stem inserter and holder. The stem inserter also comprises a handle, while the holder comprises a grip. A proximal body portion of an implant is loaded, or mounted, onto the holder. A distal stem portion of the implant is affixed onto the stem inserter. The modular hip body/stem inserter maintains the proximal body portion and distal stem portion a short distance apart to prevent these implant components from locking together (e.g., via a taper locking mechanism). The stem inserter can be adjusted, e.g., via the handle, to control the version of the distal stem, while the holder can be independently adjusted, e.g., via the grip, to control the version of the proximal body. Once the version is adjusted to determine a final seating position, the stem inserter portion of the modular hip body/stem inserter is removed and the holder is then used to impact the proximal body and distal stem together, thereby locking the implant components together through the taper locking mechanism—thus, setting the final implant seating position.

DETAILED DESCRIPTION

The inventive concept is illustrated in the context of a hip body/stem inserter used in orthopedic hip implants. As such, other than the inventive concept, familiarity with hip implants, and the components used therein, is assumed and not described further herein. (For example, a locking taper for self-locking pieces of an implant together is well known and not described herein as is a ball detent comprising a spring, ball bearing and associated groove.) In addition, it should be appreciated that the inventive concept is not limited to hip implants and applies to any implant application requiring version, or orientation, control of different portions of the implant.

Figure 1:
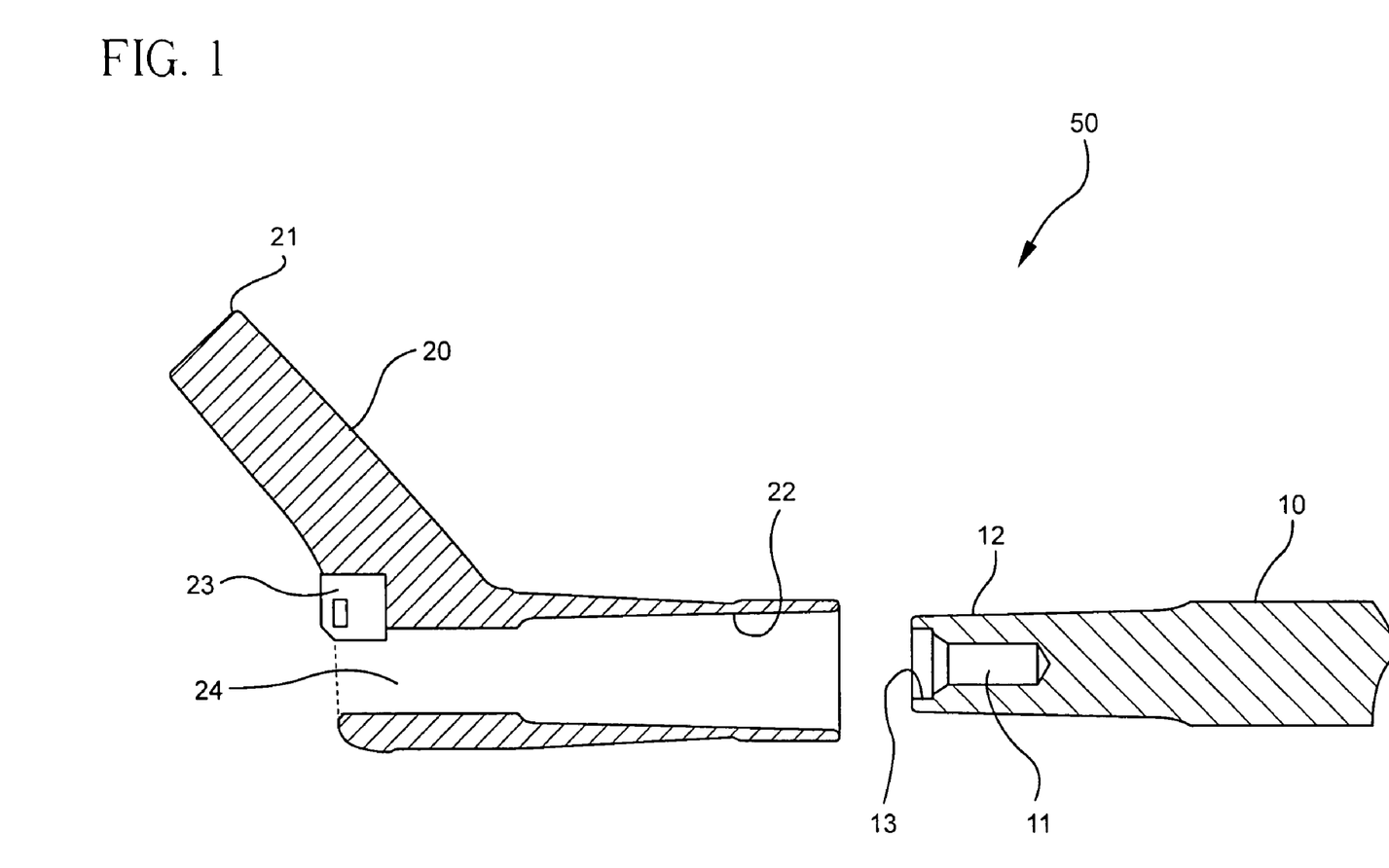
FIG. 1 shows a side cross-sectional view of a hip implant.

An illustrative hip implant 50 is shown in FIG. 1. Hip implant 50 comprises two components: a proximal body 20 and a fluted distal stem 10 (only a portion of which is shown in FIG. 1). Proximal body 20 comprises upright portion 21 for receiving a ball head (not shown), a receptacle 23, opening 24 and a tapered portion 22. Distal stem 10 also comprises a tapered portion 12. Tapered portions 12 and 22 are interlocking tapers as known in the art such that when distal stem 10 is fully seated into opening 24 of proximal body 20—distal stem 10 and proximal body 20 are locked together. Distal stem 10 further comprises female hex end 13 and threaded female portion 11 (both described further below).

Figure 2A:
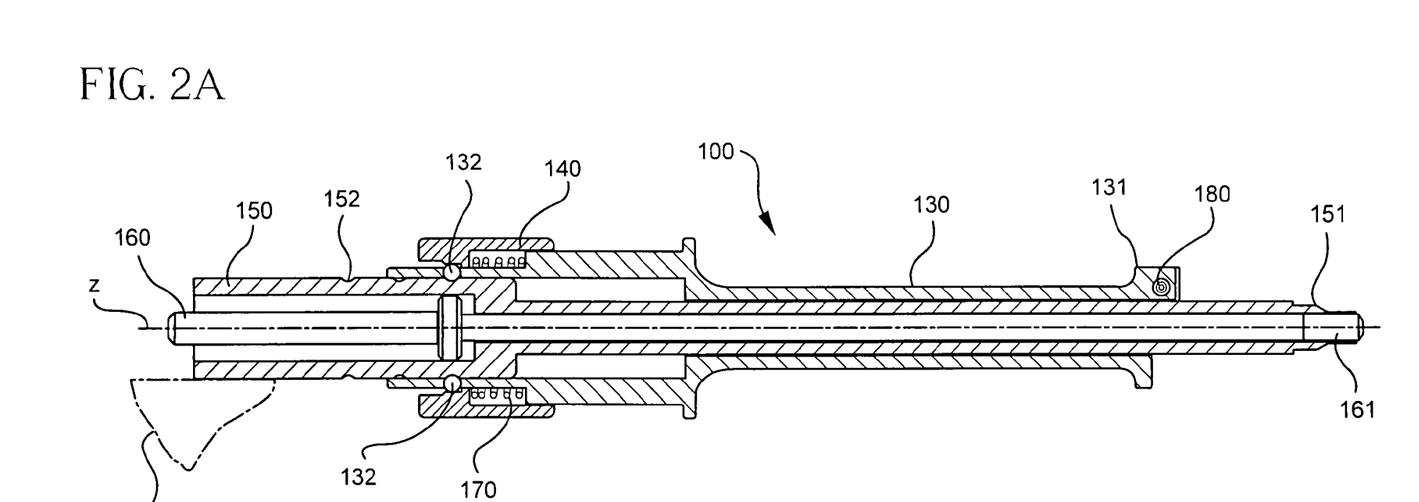
FIG. 2A shows a side cross-sectional view of an illustrative embodiment of a positioning tool in accordance with the principles of the invention.
Figure 2B:
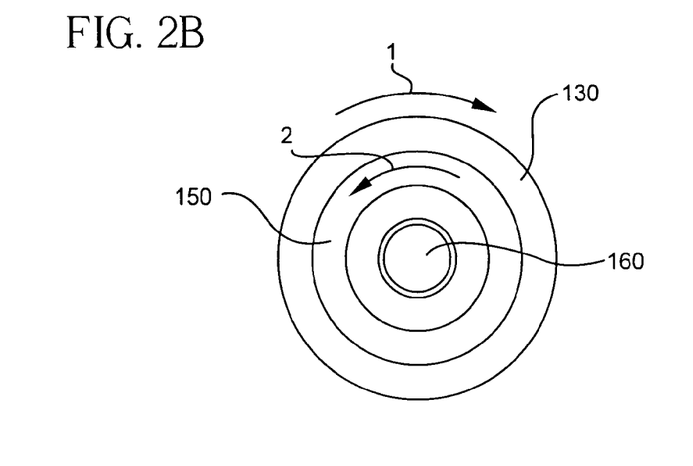
FIG. 2B shows an end view of the positioning tool shown in FIG. 2A.

An embodiment of the invention is shown in FIGS. 2A and 2B with respect to a modular hip body/stem inserter (inserter) 100. The latter is used, in accordance with one aspect of the invention, to position the hip implant 50 into a femur (not shown) such that there is independent control of the orientation of the components, or portions, of the implant, here represented by proximal body 20 and distal stem 10. In other words, during implantation the surgeon can now independently adjust the orientation of the various parts of the implant.

Inserter 100 comprises a holder (or proximal body impactor) 130, a sleeve 140, a shaft 150, a rod (or pin) 160 having a threaded male end 161 (rod 160 is hereafter referred to as threaded rod 160), a spring 170, and a ball detent 180. (Although not completely shown in FIG. 2, inserter 100 also comprises a handle 105, which is coupled to shaft 150.) In the context of this description, the term "stem inserter" refers either to shaft 150 or threaded rod 160, or their combination. (Indeed, in accordance with another aspect of the invention, shaft 150 can be easily modified to provide the functions of rod 160. Alternatively, rod 160 could be modified to provide the functions of shaft 150.)

As illustrated in FIGS. 2A and 2B, threaded rod 160 is disposed within shaft 150, which is also disposed within holder 130. Sleeve 140, which includes spring 170, surrounds holder 130 and is used to position holder 130 on shaft 150 (described further below). (It should be noted that sleeve 140 could also be integrated with holder 130.) Ball detent 180 is mounted on distal end portion 131 of holder 130. It should be observed that threaded rod 160, in the direction of distal end portion 131, extends beyond shaft 150. In addition, shaft 150 comprises, at the distal end, end 151, which is illustratively hexagon shaped (hereafter, male hex end 151). The latter mates with the female hex end 13 of distal stem 10 (described further below).

In accordance with one aspect of the invention, the position of shaft 150 with respect to holder 130 is adjustable. Shaft 150 further comprises, at the proximal end, circular grooves (as represented by groove 152) and holder 130 comprises, at the proximal end, ball detent pair 132. As can be observed from FIG. 2, if holder 130 is moved up or down on shaft 150, ball detent pair 132 will periodically engage one of the grooves of shaft 150—thus allowing the position of holder 130 with respect to shaft 150 to be adjusted in finite increments. This enables inserter 100 to accommodate different size lengths of proximal body 20 such that at least a distance d is maintained between the affixed proximal body 20 and affixed distal stem 10. As will become apparent from the description below, maintaining at least a separation distance d prevents the proximal body and the distal stem from locking together for allowing independent adjustment of their orientations. It should be noted that other equivalent forms of adjustment may be used such as, but not limited to, using threaded elements for adjustment of the shaft and holder, wire clips, etc.

As illustrated in FIGS. 2A and 2B, inserter 100 provides for independent version control about an axis z, via shaft 150, and holder 130. For example, holder 130 can be rotated in direction 1, while shaft 150 can be rotated in direction 2—thus, an adjustment to the orientation of holder 130 is independent of any adjustment to the orientation of shaft 150.

Figure 3A:
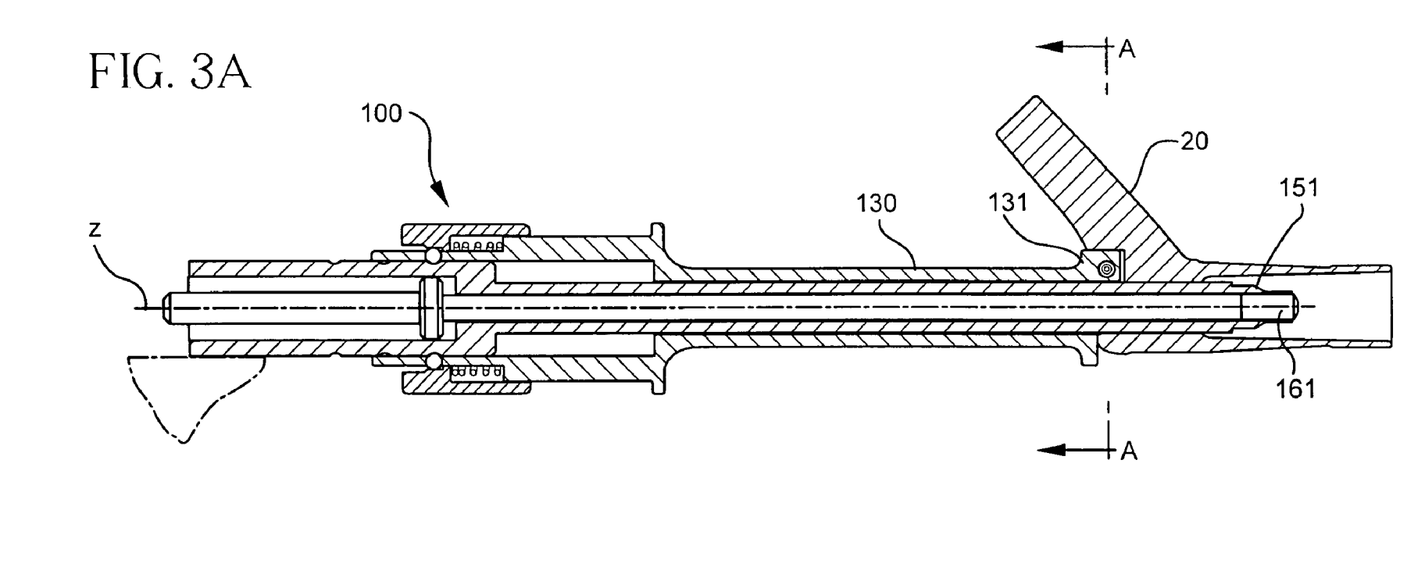
FIG. 3A is a side cross-sectional view of the positioning tool.
Figure 3B:
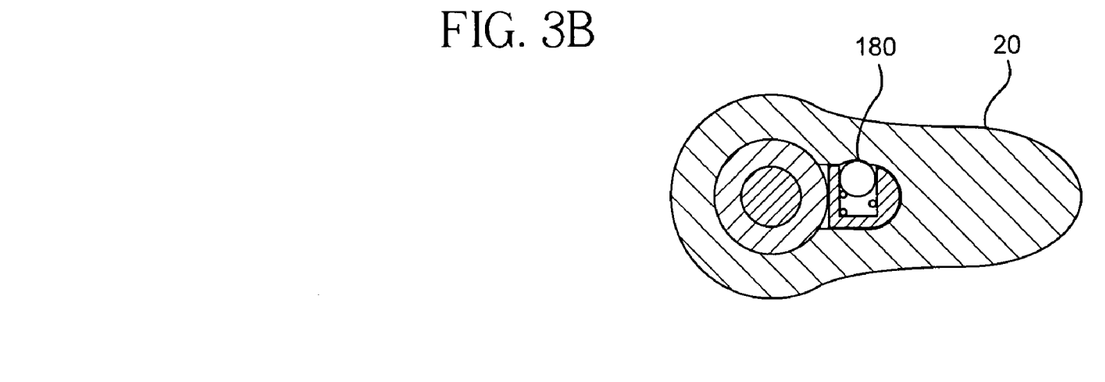
FIG. 3B is a sectional view taken along line B-B of FIG. 3.

Turning now to FIGS. 3A and 3B, a further illustration with hip implant 50 is described. In particular, proximal body 20 is first mounted to holder 130 of inserter 100 such that receptacle 23 mates with ball detent 180. The latter provides a secure, temporary, mounting of proximal body 20 to holder 130 of inserter 100. As can be observed from FIG. 3, threaded male end 161, of threaded rod 160, extends into the opening within proximal body 20 beyond shaft 150. FIG. 3B, further illustrates the use of ball detent 180 for temporarily mounting proximal body 20 onto holder 130.

Figure 4A:
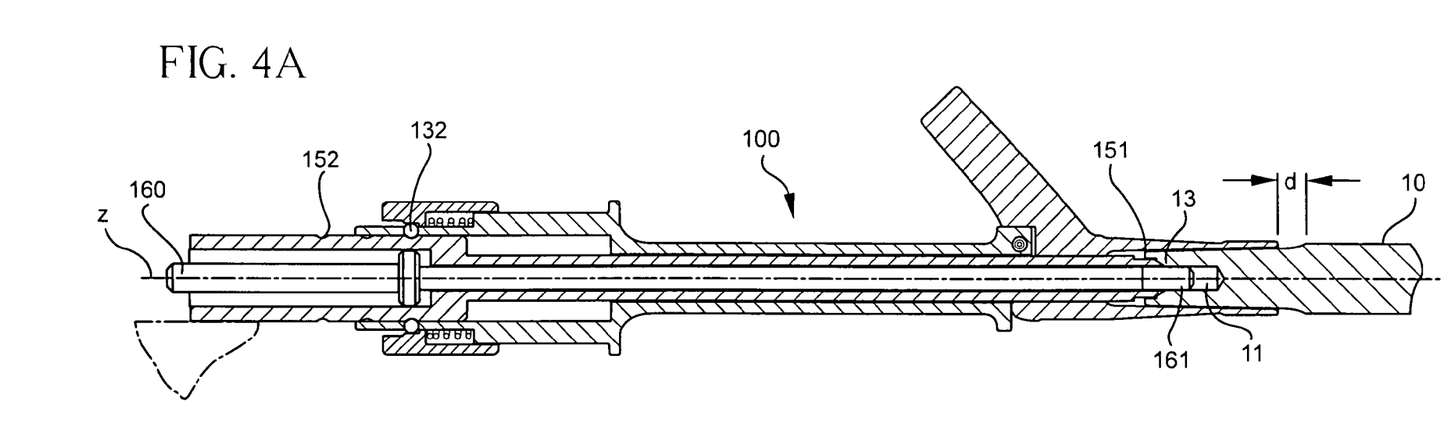
FIG. 4A is a side cross-sectional view illustrating use of a hip positioning tool with the hip implant of FIG. 1.
Figure 4B:
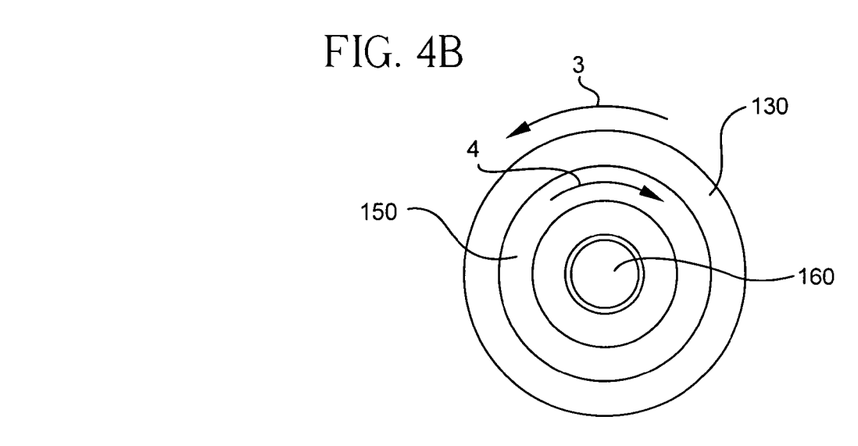
FIG. 4B is an end view of the tool shown in FIG. 4A.
Figure 5A:
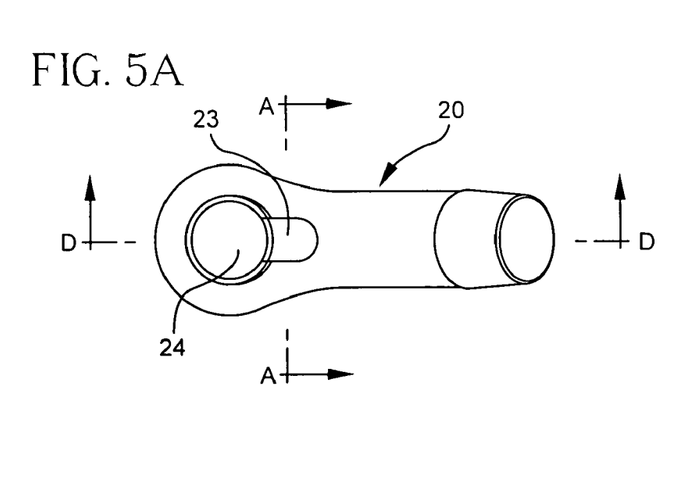
FIG. 5A shows a top plan view of the proximal body of the hip implant shown in FIG. 1.
Figure 5B:
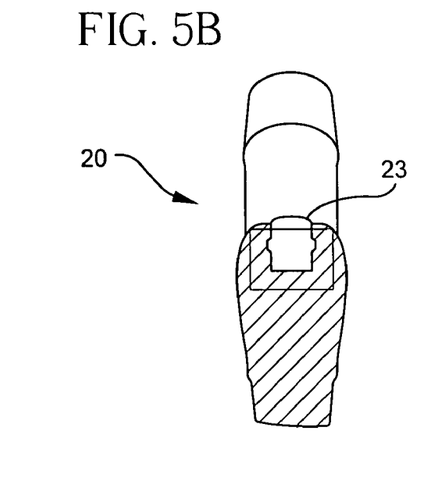
FIG. 5B is a sectional view taken along line A-A of FIG. 5A.
Figure 5C:
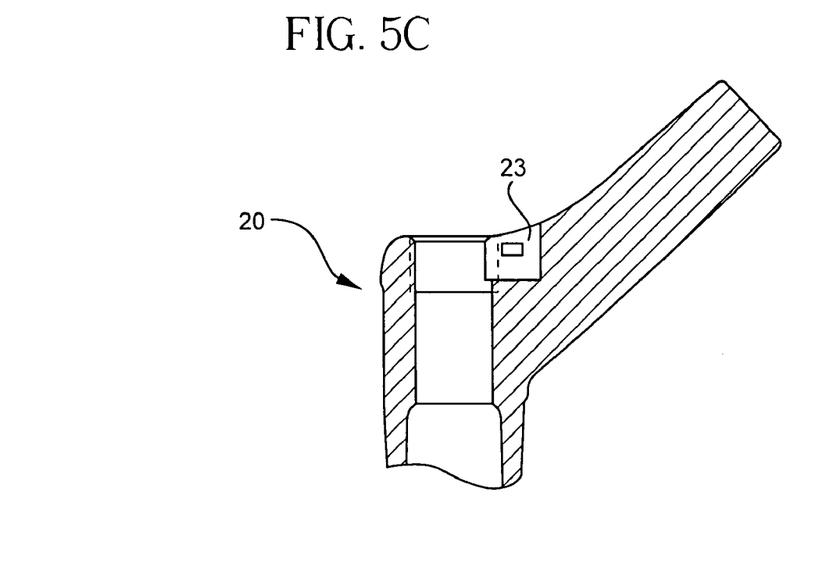
FIG. 5C is a sectional view taken along line D-D of FIG. 5A.
Figure 6A:
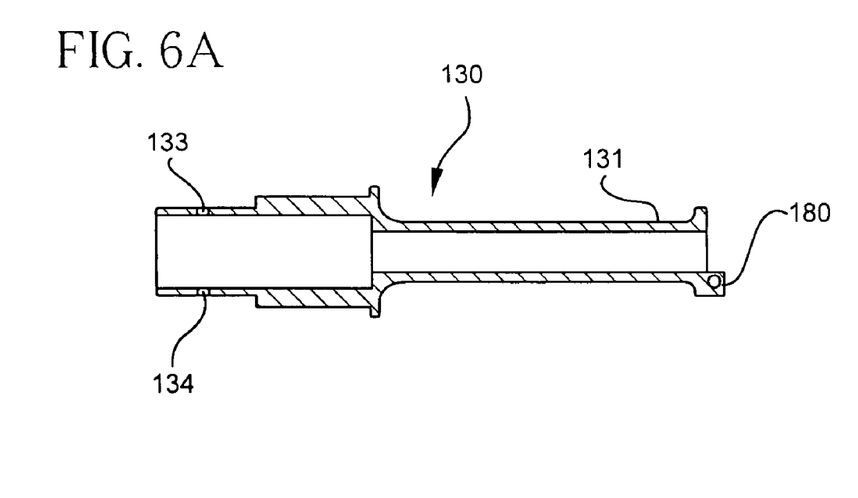
FIG. 6A shows a side cross-sectional view of the holder portion of the tool shown in FIG. 2.
Figure 6B:
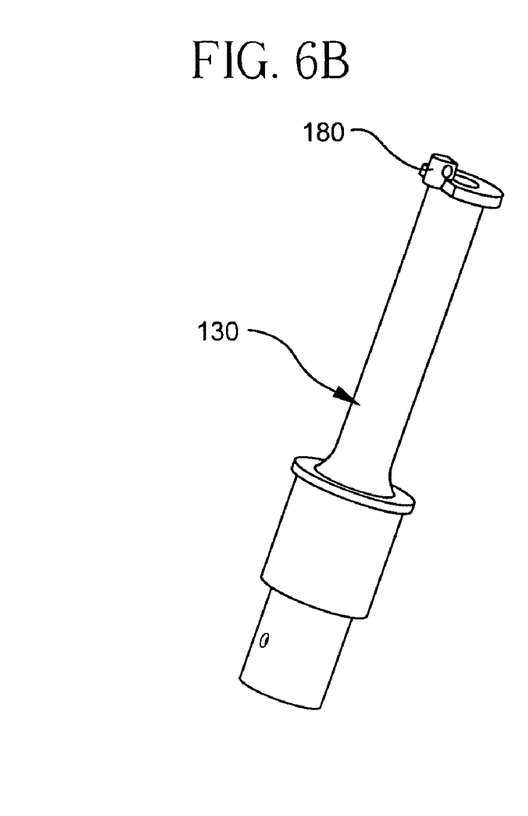
FIG. 6B is a perspective view of the holder portion at the tool shown in FIG. 2.
Figure 7A:
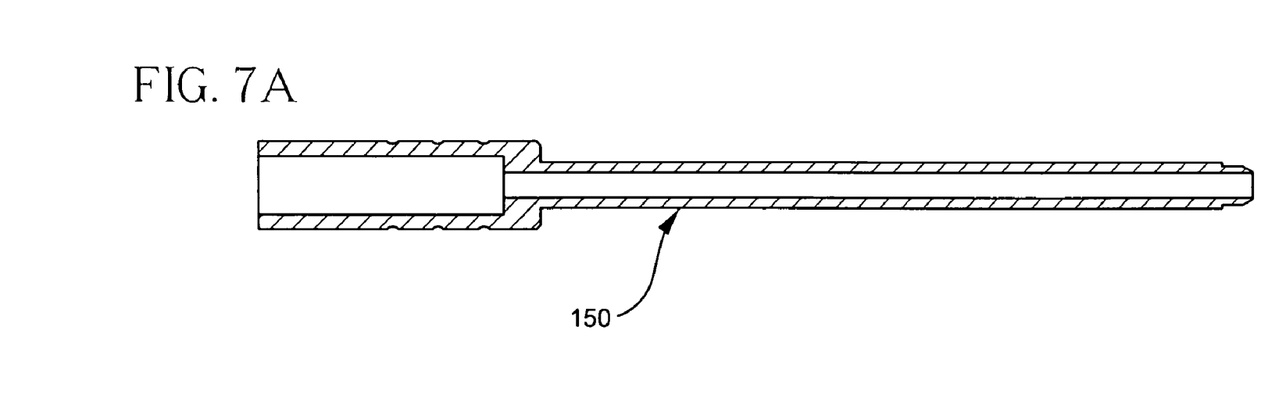
FIG. 7A is a side cross-sectional view of the shaft portion of the tool shown in FIG. 2.
Figure 7B:
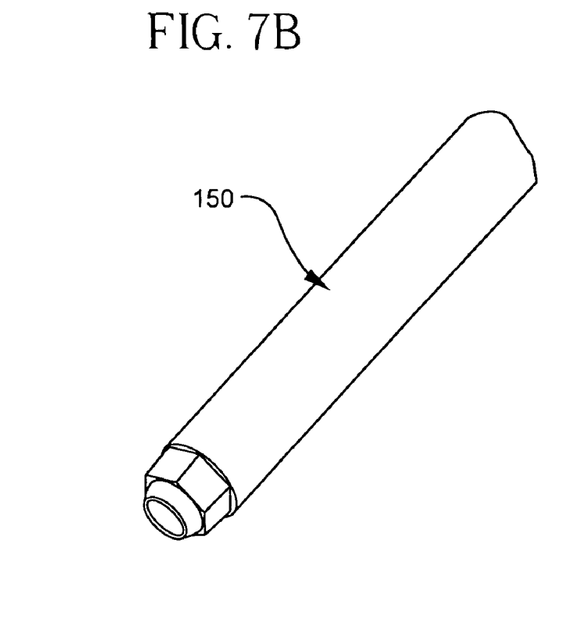
FIG. 7B is a perspective view of the shaft portion of the tool shown in FIG. 2.
Figure 7C:
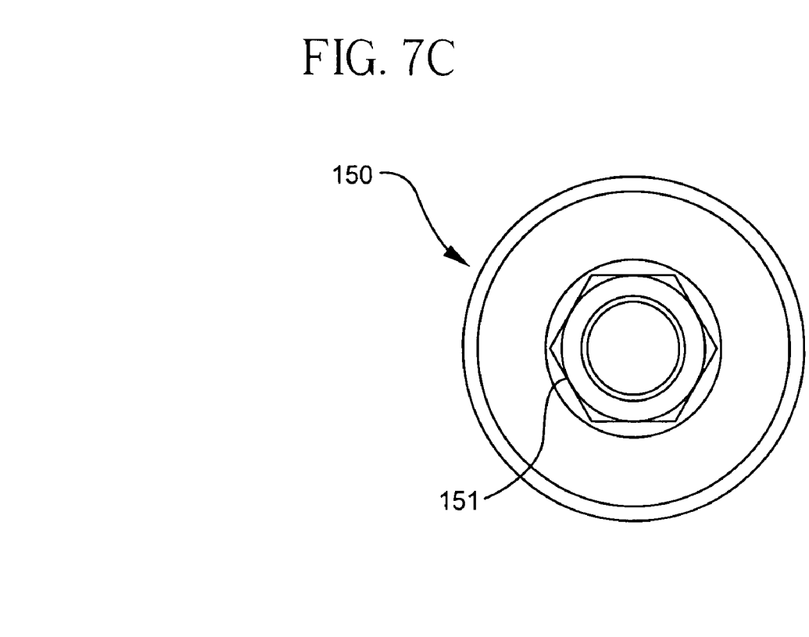
FIG. 7C is an enlarged distal end view of the shaft portion of the tool.

After mounting of proximal body 20 to holder 130 of inserter 100, distal stem 10 is attached to threaded rod 160. This is illustrated in FIGS. 4A and 4B. In particular, distal stem 10 is inserted into opening 24 of proximal body 20 such that threaded male end 161, of threaded rod 160, engages female threaded portion 11 of distal stem 10. As distal stem 10 is screwed onto threaded rod 160, female hex end 13 of distal stem 10 is drawn onto male hex end 151 of shaft 150. Once these hex ends are engaged, the implant components are rigidly held together—without taper portion 22, of proximal body 20, or taper portion 12, of distal stem 10, engaging. This is illustrated in FIG. 4A by the separation distance, d, between distal stem 10 and proximal body 20. Thus, threaded male end 161 locks distal stem 10 to inserter 100 and male hex end 151 enables shaft 150 to provide rotational control of distal stem 10, via female hex end 13. (It should be noted that other forms of attachment can be used to affix distal stem 10 to rod 160.)

As noted above, and in accordance with one aspect of the invention, inserter 100 initially maintains the taper portions of both proximal body 20 and distal stem 10 apart by at least a distance d, such that they do not lock together. Indeed, and as described above, holder 130 can slide, or move, up or down on shaft 150 for providing this separation distance for different length proximal bodies.

In this initial arrangement, the orientation of proximal body 20 is adjusted by movement, or rotation, of holder 130, in either direction about an axis z, e.g., in direction 3 of FIG. 4B. (This movement can be facilitated by placement of a grip on holder 130, or alternatively using the upright portion 21 of proximal body 20.) Since holder 130 is free to move around shaft 150—any change to the orientation of proximal body 20 via rotation of holder 130 does not affect the orientation of distal stem 10. Similarly, the orientation of distal stem 10 is adjusted by rotation of shaft 150, via handle 105, in either direction about axis z, e.g., in direction 4 of FIG. 4B—without effecting the position of proximal body 20. Thus, inserter 100 provides for independent version control of proximal body 20 and distal stem 10 as the construct is impacted (i.e., as the inserter 100 plus implant 50 is inserted into the femur). As the implant approaches the final seating position (e.g., 5 mm-mm) continual adjustments can be made to the orientations of proximal body 20 and distal stem 10. Once in the final seating position, threaded rod 160 and shaft 150 are removed, and holder 130 is then used to impact the proximal body and distal stem together (e.g., through use of a hammer), thereby locking the implant components together through the taper locking mechanism—thus, setting the final implant seating position for the assembled implant. Further impacting of holder 130 fully seats the assembled implant in the femur.

Figure 8:
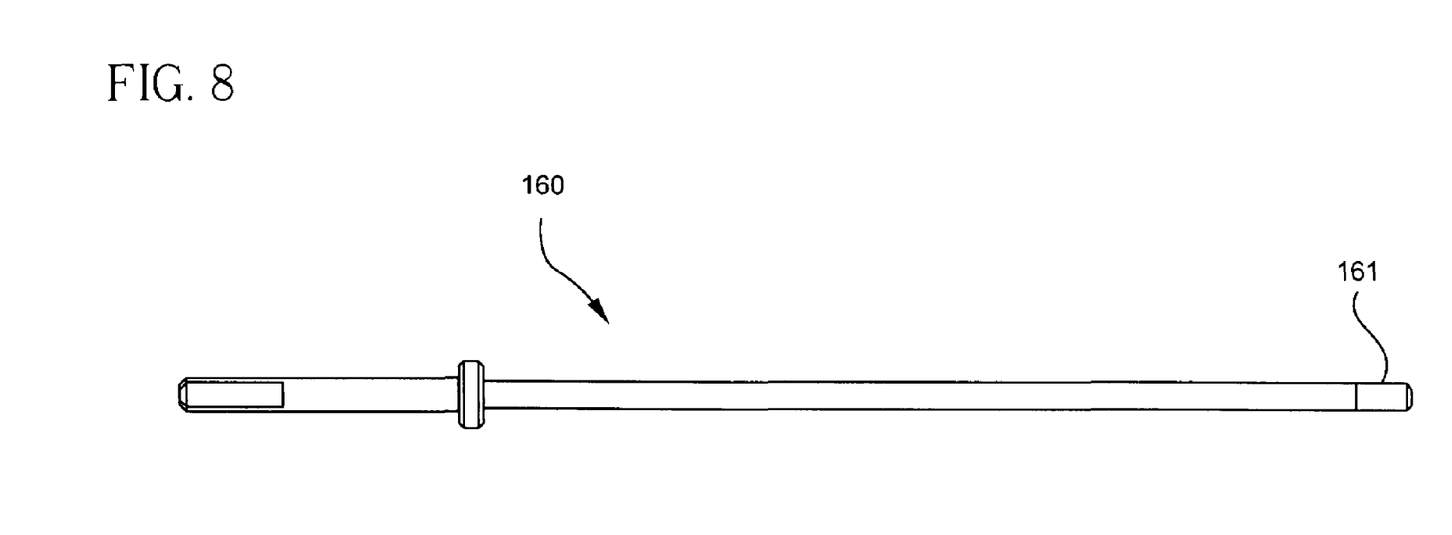
FIG. 8 shows a side cross-sectional view of threaded rod 160.
Figure 9:
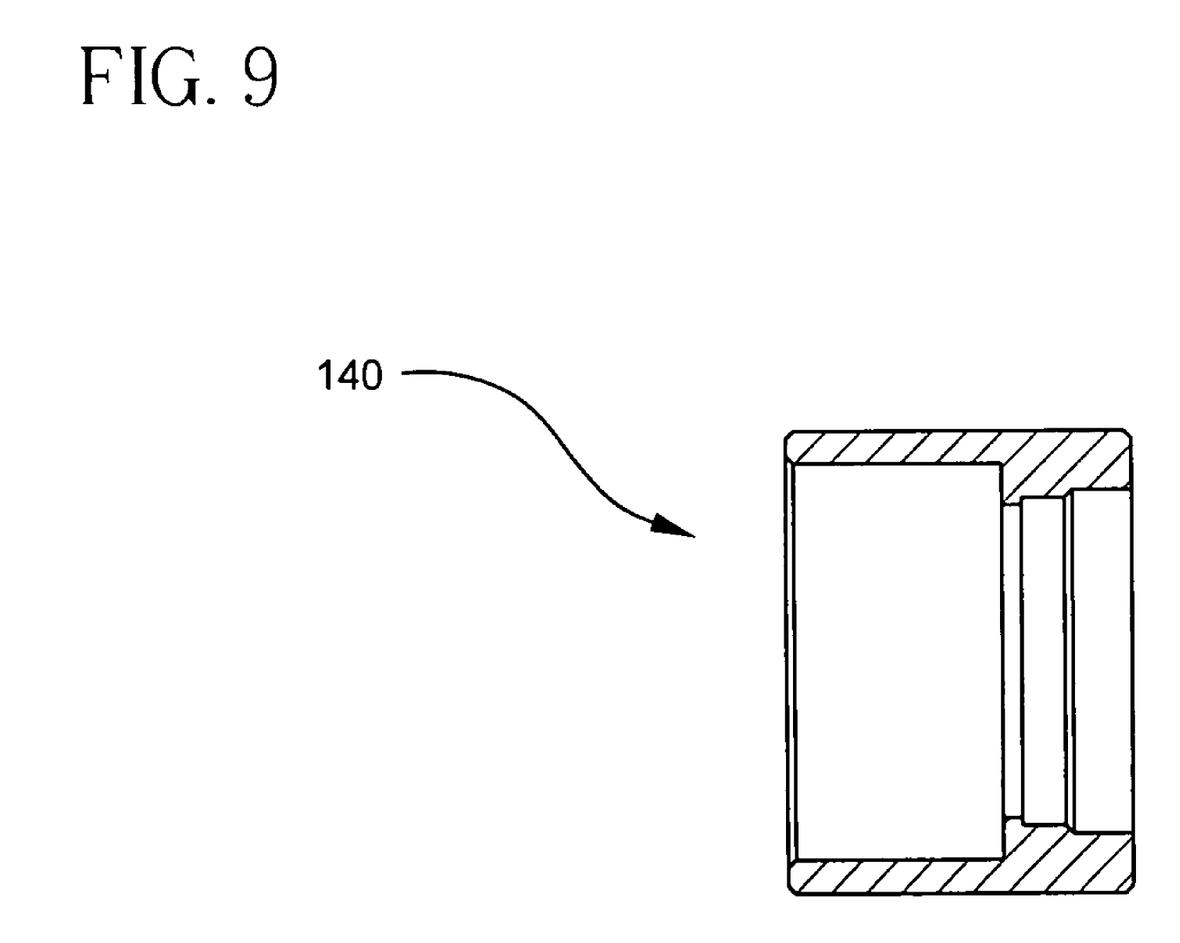
FIG. 9 shows a side cross-sectional view of the sleeve portion of the tool shown in FIG. 2.

FIGS. 5-9, provide individual views (not to scale) of the various above-described parts of implant 50 and inserter 100 for reference purposes and are not described further herein. FIGS. 5A-C show proximal body 20 of the implant 50 in top plan and sectional views. FIGS. 6A and 6B illustrate holder 130 with locations 133 and 134 for ball detent pair 132. FIGS. 7A-C show various views of shaft 150, illustrating male hex end 151. FIG. 8 illustrates threaded rod 160. FIG. 9 shows sleeve 140.

Thus, as described above and in accordance with one aspect of the invention, the modular hip body/stem inserter with independent version control of body and stem rectifies the problem of neck version control on modular implants by allowing the proximal body and the distal stem to be implanted simultaneously while independently controlling the version, or orientation, of the proximal body and distal stem.

Although the invention herein has been described with reference to particular embodiments, it is to be understood that these embodiments are merely illustrative of the principles and applications of the present invention. For example, other forms of attachment or locking mechanisms such as the above-illustrated ball detent, may be used, such as screws, etc. In addition, the functions provided by rod 160 and shaft 150 can be integrated into one component. It is therefore to be understood that numerous modifications may be made to the illustrative embodiments and that other arrangements may be devised without departing from the spirit and scope of the present invention as defined by the appended claims.

The invention claimed is:

1. A positioning tool for placing an orthopedic implant having a first and a second component, the tool comprising:
  a first piece having an engagement element thereon configured to engage, rotate with, and control the orientation of the first component of the implant and having a detent element, wherein the engagement element of the first piece directly engages the first component on an axis of rotation of the first piece and first component;
  a second piece rotatably mounted on the first piece for rotation about the axis of rotation of the first piece and first component and configured to engage and control the orientation of the second component of the implant, about the axis of rotation of the first piece, second piece and first component, and having an adjustment feature at a plurality of axial positions along a shaft of the second piece which engages the detent element of the first piece to secure the first and second pieces at a plurality of axial positions along the shaft of the second piece, the first and second pieces configured so that adjustments to a rotational orientation of the first piece and the second piece are independent of each other, and the tool provides independent version control for the engaged first component of the implant and the engaged second component of the implant, wherein the axis of rotation between the first piece and second piece is coaxial.

2. The positioning tool of claim 1 wherein the second piece comprises a third piece and a fourth piece, wherein the third piece is configured to control orientation of the engaged second component and the fourth piece is configured to lock the engaged second component to the third piece.

3. The positioning tool of claim 1, wherein the positioning tool provides at least a minimal separation between the engaged first component of the implant and the engaged second component of the implant to prevent locking of these implant components together while adjusting any orientation of the implant components.

4. The positioning tool of claim 3, wherein the first piece is capable of moving the second piece up or down to affect a value of the minimal separation distance.

5. The positioning tool of claim 1, wherein the engaging features comprises a ball detent.

6. The positioning tool of claim 5, wherein the adjustment features comprises at least one recess positioned latitudinally on the outer surface of the shaft for receiving the ball detent.

7. A positioning tool for placing an orthopedic implant, the tool comprising:
  a first rotatable piece having an engagement element thereon for changing an orientation and directly engaging a first component of the implant on an axis of rotation of the first piece and first component for rotation therewith about the axis of rotation of the first piece and the first component and having a detent element;
  a second piece rotatably mounted on the first piece for rotation about the axis of rotation of the first piece and first component and for engaging a second component of the implant on the axis of rotation of the first piece, second piece and first component and having an adjustment feature at a plurality of axial positions along a shaft of the second piece which engages the detent element of the first piece to secure the first and second pieces at a plurality of axial positions along the shaft of the second piece; and
  a third rotatable piece rotatable with said second component for changing an orientation of the implant about the axis of rotation of the first piece, second piece, first component and second component, such that the change in orientation provides version control for the engaged second component, wherein rotation of the first piece or the third piece does not affect the orientation of the other of the first piece or third piece, said first piece, said second piece, and said third piece having an axis of rotation which is coaxial with one another.

8. The positioning tool of claim 7, wherein the third piece is a shaft which is inserted into the first piece and the second piece is a rod, which is inserted into the shaft for locking onto the second component such that the shaft provides rotational control for the engaged second component.

9. The positioning tool of claim 7, wherein the engaging features comprises a ball detent.

10. The positioning tool of claim 9, wherein the adjustment features comprises at least one recess positioned latitudinally on the outer surface of the shaft for receiving the ball detent.

11. A positioning tool for placing an orthopedic implant, the implant comprising a proximal body and a distal stem, the tool comprising:
  a first piece comprising a holder having an engagement element thereon configured to be directly affixed to the proximal body of the implant on an axis of rotation of the first piece and proximal body, the first piece having an aperture extending therethrough and having a detent element; and
  a second piece comprising a stem inserter rotatably mounted on the first piece for rotation about the axis of rotation of the first piece and proximal body and configured to directly affix to the distal stem of the implant on the axis of rotation of the first piece, second piece and proximal body for rotation therewith on the axis and having an adjustment feature at a plurality of axial positions along a shaft of the second piece which engages the detent element of the first piece to secure the first and second pieces at a plurality of axial positions along the shaft of the second piece, wherein the positioning tool provides independent version control of the affixed proximal body and the affixed distal stem, wherein the second piece is disposed within the aperture of the first piece.

12. The positioning tool of claim 11 wherein the stem inserter comprises a shaft.

13. The positioning tool of claim 11 wherein the stem inserter comprises a rod.

14. The positioning tool of claim 11 wherein the second piece comprises a shaft and a rod, wherein the rod is configured to affix the distal stem to the positioning tool and the shaft provides version control of the distal stem.

15. The positioning tool of claim 11 wherein the holder is capable of sliding the stem inserter up or down to adjust the separation distance of the affixed proximal body and the affixed distal stem, and the separation distance prevents locking of the affixed proximal body to the affixed distal stem while providing the independent version control.

16. The positioning tool of claim 11, wherein the proximal body comprises a first taper and the distal stem comprises a second taper, and the proximal body, when affixed, and the distal stem, when affixed, are maintained a distance apart from each other by the positioning tool such that the first and the second tapers do not lock together.

17. The positioning tool of claim 11, wherein the holder further comprises a locking mechanism configured to affix the proximal body onto the holder.

18. The positioning tool of claim 11, wherein the locking mechanism includes a ball detent.

19. The positioning tool of claim 11, wherein adjustment of the stem inserter controls a version of the distal stem, while adjustment of the holder independently controls a version of the proximal body.

20. The positioning tool of claim 19, wherein the adjustment of the stem inserter is performed via a handle attached to a portion of the stem inserter.

21. The positioning tool of claim 11, wherein the engaging features comprises a ball detent.

22. The positioning tool of claim 21, wherein the adjustment features comprises at least one recess positioned latitudinally on the outer surface of the shaft for receiving the ball detent.

23. A positioning tool comprising:
a shaft having a distal end, the shaft is rotatably mounted on a holder for rotation about an axis of rotation and adapted to directly engage a distal stem portion of an implant on the axis of rotation of the shaft and having an adjustment feature at a plurality of axial positions along the shaft;
the holder having a distal end, the holder having an engagement element thereon adapted to directly mount a proximal body portion of the implant on the distal end of the holder on the axis of rotation of the shaft and distal stem and having a detent element which engages the adjustment feature of the shaft and secures the holder and proximal body portion at a plurality of axial positions along the shaft; and
a rod having a distal end, the rod adapted to directly mount the distal stem portion for engagement and rotation by the shaft on the axis of rotation of the shaft, holder, proximal body and distal stem, wherein the rod is inserted into the shaft and the shaft is inserted into the holder and wherein the shaft rotates independent of any rotation of the holder, providing independent version control of the distal stem portion of the implant with respect to the proximal body portion of the implant, wherein the axis of rotation between the rod, shaft and holder is coaxial.

24. The positioning tool of claim 23, wherein the rod mounts the distal stem portion of the implant via respective threaded portions.

25. The positioning tool of claim 23, wherein the holder mounts the proximal body portion of the implant via a ball detent arrangement.

26. The positioning tool of claim 23, wherein the mounted distal stem portion of the implant and the mounted proximal body portion of the implant are maintained a separation distance apart for preventing locking of the distal stem portion to the proximal body portion.

27. The positioning tool of claim 26 wherein the holder is capable of sliding up and down the shaft for adjustment of the separation distance.

28. The positioning tool of claim 23, wherein the engaging features comprises a ball detent.

29. The positioning tool of claim 28, wherein the adjustment features comprises at least one groove positioned latitudinally around the outer surface of the shaft for receiving the ball detent.

* * * * *